United States Patent
Isab et al.

(10) Patent No.: US 10,494,392 B2
(45) Date of Patent: *Dec. 3, 2019

(54) METHOD OF TREATING CANCER WITH A TWO-COMPONENT ANTI-CANCER COMPOSITION

(71) Applicant: KING FAHD UNIVERSITY OF PETROLEUM AND MINERALS, Dhahran (SA)

(72) Inventors: Anvarhusein A. Isab, Dhahran (SA); Muhammad Altaf, Dhahran (SA); Adam Ahmed Abdallah Seliman, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,355

(22) Filed: May 6, 2019

(65) Prior Publication Data

US 2019/0256537 A1 Aug. 22, 2019

Related U.S. Application Data

(63) Continuation of application No. 15/807,827, filed on Nov. 9, 2017, now Pat. No. 10,336,779.

(60) Provisional application No. 62/486,169, filed on Apr. 17, 2017.

(51) Int. Cl.
| | |
|---|---|
| *A61K 31/80* | (2006.01) |
| *C07F 9/50* | (2006.01) |
| *C07F 1/12* | (2006.01) |
| *C08G 79/00* | (2006.01) |

(52) U.S. Cl.
CPC ............ *C07F 9/5045* (2013.01); *A61K 31/80* (2013.01); *C07F 1/12* (2013.01); *C08G 79/00* (2013.01)

(58) Field of Classification Search
CPC ... C07F 9/50; C07F 1/12; C08G 79/00; A61K 31/80
See application file for complete search history.

(56) References Cited

PUBLICATIONS

Benoît Bertrand, et al., "Gold(I) NHC-based homo- and heterobimetallic complexes: synthesis, characterization and evaluation as potential anticancer agents", Journal of Biological Inorganic Chemistry, vol. 20, No. 6, 2015, pp. 1005-1020.
Semra Tasan, et al., "Gold-phosphine-porphyrin as potential metal-based theranostics", Journal of Biological Inorganic Chemistry, vol. 20, No. 1, 2015, pp. 143-154.
Pierre-Emmanuel Doulain, et al., "Towards the elaboration of new gold-based optical theranostics", Dalton Transactions, vol. 44, No. 11, Mar. 21, 2015, pp. 4874-4883.
Benoît Bertrand, et al., "Gold(I) N-heterocyclic carbene complexes with an "activable" ester moiety: Possible biological applications", Journal of Organometallic Chemistry, vol. 775, 2015, pp. 124-129.
Nathalie Dupré, et al., "Self-Buffering Hybrid Gold-Polyoxometalate Catalysts for the Catalytic Cyclization of Acid-Sensitive Substrates", Chemistry—A European Journal, vol. 18, No. 41, 2012, pp. 12962-12965.
Damian Paliwoda, et al., "Unwinding $Au^+$—$Au^+$ Bonded Filaments in Ligand-Supported Gold(I) Polymer under Pressure", The Journal of Physical Chemistry Letters, vol. 5, 2014, pp. 2182-2188.
Giulia Boscutti, et al., "Insights into the Reactivity of Gold-Dithiocarbamato Anticancer Agents toward Model Biomolecules by Using Muitinuclear NMR Spectroscopy", Chemistry—A European Journal, vol. 19, Issue 40, Sep. 27, 2013, pp. 13428-13436 (Abstract only).
Junzhao Liao, et al., "Theoretical study on the bifunctional substitution reactions between gold(III) dithiocarbamate derivative $Au(DMDT)Cl_2$ (DMDT = N,N-dimethyldithiocarbamate) and target molecules", Computational and Theoretical Chemistry, vol. 1048, Nov. 15, 2014, pp. 84-94 (Abstract oniy).
Muhammad Altaf, et al., "Synthesis, characterization and in vitro cytotoxicity of gold(III) dialkyl/diaryldithiocarbamato complexes", RSC Advances, vol. 5, 2015, pp. 81599-81607.
T. Srinivasa Reddy, et al., "Anti-cancer gold(I) phosphine complexes: Cyclic trimers and tetramers containing the P—Au—P moiety", Journal of Inorganic Biochemistry, vol. 175, Oct. 2017, pp. 1-8 (Abstract only).
Jiří Schulz, et al., "Synthesis, structural characterization and cytotoxicity of bimetallic chlorogold(I) phosphine complexes employing functionalized phosphinoferrocene carboxamides", Journal of Organometallic Chemistry, vol. 751, Feb. 2014, pp. 604-609 (Abstract only).

*Primary Examiner* — Zohreh A Fay
(74) *Attorney, Agent, or Firm* — Oblon, McClelland, Maier & Neustadt, L.L.P.

(57) ABSTRACT

Gold(I) complexes and gold(I) dithiocarbamate polymers as anticancer therapeutics. The Au(I) ion within the gold(I) complexes is coordinated to two phosphine ligands. The repeating unit formed by Au(I) ion coordinating to dithiocarbamate ligands are connected by Au(I)—Au(I) interactions within the gold(I) dithiocarbamate polymers. Also disclosed are methods of synthesis, pharmaceutical compositions incorporating the gold(I) complexes, pharmaceutical compositions incorporating the gold(I) dithiocarbamate polymers, and methods of treating cancer.

3 Claims, 4 Drawing Sheets

METHOD OF TREATING CANCER WITH A TWO-COMPONENT ANTI-CANCER COMPOSITION

CROSS REFERENCE TO RELATED APPLICATIONS

The present application is a Continuation of Ser. No. 15/807,827, now allowed, having a filing date of Nov. 9, 2017 which claims benefit of priority to U.S. provisional application No. 62/486,169 having a filing date of Apr. 17, 2017 which is incorporated herein by reference in its entirety.

STATEMENT OF FUNDING ACKNOWLEDGEMENT

This project was funded by the National Plan for Science and Innovation (MARIFAH)-King Abdulaziz City for Science and Technology (KACST) through the Science and Technology Unit at King Fahd University of Petroleum and Minerals (KFUPM) of Saudi Arabia, award No. 14-MED64-4.

STATEMENT REGARDING PRIOR DISCLOSURE BY THE INVENTORS

Aspects of this technology are described in an article "Synthesis, Characterization and in vitro Cytotoxicity of Gold(I) Complexes of 2-(Diphenylphosphanyl)ethylamine and Dithiocarbamates" published in Journal of Inorganic and General Chemistry, 2016, 642, (24), 1454-1459, on Nov. 3, 2016, which is incorporated herein by reference in its entirety.

BACKGROUND OF THE INVENTION

Technical Field

The present invention relates to therapeutic gold(I) complexes, a pharmaceutical composition thereof, and a method of treating cancer. The present invention further relates to therapeutic gold(I) dithiocarbamate polymers, a pharmaceutical composition thereof, and a method of treating cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The discovery of antitumor properties of cisplatin (B. Rosenberg et al., Nature. 1965, 205, 698-699; S. J. Lippard et al., Chem. Rev. 2016, 116, 3436-3486; and S. M. A. Zoroddu et al., Coord Chem. Rev. 2015, 284, 329-350, each incorporated herein by reference in their entirety) has triggered a great deal of interest in the field of anticancer metallodrugs (C. G. Hartinger et al., Drug Discov. Today, 2014, 19, 1640-1648; C. M. Che et al., Dalton Trans. 2007, 4884-4892: A. A. Isab et al., Polyhedron 2006, 25, 1633-1645; A. Filipovska et al., Metallomics, 2011, 3, 863-873; C. Nardon et al., Anticancer Res. 2014, 34, 487-492; L. Rodriguez et al., Anticancer Agents Med. Chem. 2011, 11, 921-928: A. Casini et al., Dalton Trans. 2014, 43, 4209-4219; E. R T. Tiekink, Crit. Rev. Oncol. Hematol. 2002, 42, 225-248; M. L. Messori et al., Gold Bulletin 2007, 40, 73-81; J. Ruiz et al., Coord. Chem. Rev. 2013, 257, 2784-2797; C. M. Che et al., Chem. Soc. Rev. 2015, 44, 8786-8801; M. Altaf et al., J. Organomet Chem. 2014, 765, 68-79; D. Fregona et al., Inorg. Chem. 2005, 44, 1867-1881; L. Cattaruzza et al., Int. J. Cancer 2011, 128, 206-215; and C. Marzano et al., Int. J. Cancer 2011, 129, 487-496, each incorporated herein by reference in their entirety). In this regard, gold(I) and gold(III) complexes have received considerable attention (C. F. III Shaw, Chem. Rev. 1999, 99, 2589-2600, incorporated herein by reference in its entirety) as they demonstrate different mechanisms of cytotoxic action than cisplatin (A. Gautier et al., Metallomics 2012, 4, 23-32, incorporated herein by reference in its entirety). Furthermore, some gold(I) complexes such as Auranofin and Myocrisin have already been used frequently for the treatment of rheumatoid arthritis. Extensive in vitro and in vivo studies have revealed satisfactory anticancer properties of many antirheumatic gold(I)-phosphine complexes including Auranofin (S. H. Park et al., Int. J. Oncol. 2014, 45, 1691-1698; and C. K. Mirabelli et al., Cancer Res. 1985, 45, 32-39, each incorporated herein by reference in their entirety). Despite these recent advances (S. J. Berners-Price et al., J. Med Chem. 1990, 33, 1386-1392; S. J. Berners-Price et al., Cancer Res. 1986, 46, 5486-5493; P. C. Healy et al., J. Inorg. Biochem. 2010, 104, 625-631; F. Caruso et al., J. Med. Chem. 2003, 46, 1737; F. Caruso et al., Biochem. Pharmacol. 2007, 73, 773-781; V. Gandin et al., Biochem. Pharmacol. 2010, 79, 90-101; K. K. Ooi et al., J. Biol. Inorg. Chem. 2015, 20, 855-873; O. Rackham et al., Biochem. Pharmacol. 2007, 74, 992-1002; G. Lupidi et al., J. Inorg. Biochem. 2013, 124, 78-87; J. D. Chaves et al., Inorg. Chim. Acta 2014, 414, 85-90; H. Scheffler et al., Polyhedron 2010, 29, 66-69; M. Ali et al., J. Med. Chem. 2015, 58, 4521-4528; Y. Wang et al., J. Med. Chem. 2013, 56, 1455-1466; R. Hayashi et al., J. Inorg. Biochem. 2014, 137, 109-114; F. K. Keter et al., Inorg Chem. 2014, 53, 2058-2067; and M. Altaf et al., Eur. J. Med. Chem. 2015, 95, 464-472, each incorporated herein by reference in their entirety), there remains a need to develop more efficient gold(I) anticancer drugs.

In view of the forgoing, one objective of the present invention is to provide a therapeutic gold(I) complex, a composition comprising the gold(I) complex, and a method of treating cancer. Another objective of the present invention is to provide a therapeutic gold(I) dithiocarbamate polymer, a composition comprising the gold(I) dithiocarbamate polymer, and a method of treating cancer.

BRIEF SUMMARY OF THE INVENTION

A first aspect of the disclosure relates to a gold(I) complex of formula (I):

or a salt thereof, a solvate thereof, a tautomer thereof, a stereoisomer thereof, or a mixture thereof, where $R_1$, $R_2$, $R_3$, and $R_4$ are independently selected from the group consisting of a hydrogen, an optionally substituted alkyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro;

$R_5$, $R_6$, $R_7$, $R_8$, $R_9$, $R_{10}$, $R_{11}$, and $R_{12}$ are independently selected from the group consisting of a hydrogen, an optionally substituted alkyl, an optionally substituted cycloalkyl, an optionally substituted aryl, and an optionally substituted arylalkyl; and X is an anion.

In one embodiment, the anion is a halide ion, a trifluoromethanesulfonate ion, a hexafluorophosphate ion, a tetrafluoroborate ion, or a perchlorate ion.

In one embodiment, $R_1$, $R_2$, $R_3$, $R_4$, $R_5$, $R_6$, $R_7$, $R_8$, $R_9$, $R_{10}$, $R_{11}$, and $R_{12}$ are a hydrogen, and the anion is Cl$^-$.

A second aspect of the disclosure relates to a composition having the gold(I) complex of formula (I) of the first aspect, and a pharmaceutically acceptable carrier and/or excipient.

In one embodiment, the composition has 0.01-100 µM of the gold(I) complex relative to the total volume of the composition.

In one embodiment, the pharmaceutically acceptable carrier and/or excipient is at least one selected from the group consisting of an organic solvent, an inorganic salt, a surfactant, and a polymer.

A third aspect of the disclosure relates to a method of treating cancer, including administering the composition of the second aspect to a subject in need of therapy.

In one embodiment, the cancer is at least one selected from the group consisting of lung cancer, colon cancer, and breast cancer.

In one embodiment, the cancer is resistant to cisplatin.

In one embodiment, 1-300 mg/kg of gold(I) complex of formula (I) is administered per body weight of the subject.

A forth aspect of the disclosure relates to a gold(I) dithiocarbamate polymer of formula (II):

or a salt thereof, a solvate thereof, a tautomer thereof, a stereoisomer thereof, or a mixture thereof.

where $R_{13}$, $R_{14}$, $R_{15}$, and $R_{16}$ are independently selected from the group consisting of a hydrogen, an optionally substituted alkyl, an optionally substituted cycloalkyl, an optionally substituted aryl, and an optionally substituted arylalkyl;

n is an integer between 2-10000; and with the proviso that $R_{13}$, $R_{14}$, $R_{15}$, and $R_{16}$ are not each an ethyl.

In one embodiment. $R_{13}$, $R_{14}$, $R_{15}$, and $R_{16}$ are independently an optionally substituted alkyl or an optionally substituted arylalkyl.

In one embodiment, $R_{13}$, $R_{14}$, $R_{15}$, and $R_{16}$ are a methyl or a benzyl.

A fifth aspect of the disclosure relates to a composition having the gold(I) dithiocarbamate polymer of formula (II) of the forth aspect and a pharmaceutically acceptable carrier and/or excipient.

In one embodiment, the pharmaceutically acceptable carrier and/or excipient is at least one selected from the group consisting of an organic solvent, an inorganic salt, a surfactant, and a polymer.

In one embodiment, the composition has 0.01-100 µM of the gold(I) dithiocarbamate polymer of formula (II) relative to the total volume of the composition.

A sixth aspect of the disclosure relates to a method of treating cancer, including administering a gold(I) dithiocarbamate polymer of formula (II), or a salt thereof, a solvate thereof, a tautomer thereof, a stereoisomer thereof, or a mixture thereof, to a subject in need of therapy, where $R_{13}$, $R_{14}$, $R_{15}$, and $R_{16}$ are independently selected from the group consisting of a hydrogen, an optionally substituted alkyl, an optionally substituted cycloalkyl, an optionally substituted aryl, and an optionally substituted arylalkyl; and n is an integer between 2-10000.

In one embodiment, the cancer is at least one selected from the group consisting of lung cancer, colon cancer, and breast cancer.

In one embodiment, the cancer is resistant to cisplatin.

In one embodiment, 1-400 mg/kg of gold(I) dithiocarbamate polymer of formula (II) is administered per body weight of the subject.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

As used herein, the terms "compound" and "complex" are used interchangeably, and are intended to refer to a chemical entity, whether in a solid, liquid or gaseous phase, and whether in a crude mixture or purified and isolated.

Unless otherwise specified, "a" or "an" means "one or more".

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethyl formamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautormers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers or both.

Conformers (rotamers), or conformational isomerism refers to a form of isomerism that describes the phenomenon of molecules with the same structural formula but with different shapes due to rotations about one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation about the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to replacing at least one hydrogen atom of a molecule with a non-hydrogen functional group. Such non-hydrogen functional groups can independently include, for example, one or more of the following: alkyl (as defined hereinafter), cycloalkyl (as defined hereinafter), aroyl (as defined hereinafter), alkoxy (i.e. straight or branched chain alkoxy includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy), alkenyl (which includes hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like), aryl (as defined hereinafter), aryloxy (e.g., phenoxy, and phenoxy substituted with halogen, alkyl, alkoxy, and/or haloalkyl such as fluoromethyl, chloromethyl, bromomethyl, iodomethyl, 2-fluoroethyl, 2-chloroethyl, 2-bromoethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl), arylalkyl (as defined hereinafter), aryloxyalkyl (e.g., phenyloxyalkyl), arylacetamidoyl, alkylaryl, heteroarylalkyl, alkylcarbonyl and arylcarbonyl or other such acyl group, heteroarylcarbonyl, or heteroaryl group, cyano, nitro, halogen (as defined hereinafter), and the like, or mixtures thereof.

As used herein, the term "alkyl" refers to a fully saturated branched, or unbranched hydrocarbon fragment. Representative examples of such alkyl include, but are not limited to, methyl, ethyl, n-propyl, isopropyl, n-butyl, sec-butyl, isobutyl, tert-butyl, n-pentyl, isopentyl, neopentyl, n-hexyl, isohexyl, 3-methylhexyl, 2,2-dimethylpentyl, 2,3-dimethylpentyl, n-heptyl, n-octyl, n-nonyl, n-decyl and the like.

As used herein, the term "cycloalkyl" refers to saturated or unsaturated monocyclic, bicyclic or tricyclic alkyl groups. Exemplary monocyclic alkyl groups include, but are not limited to, cyclopropyl, cyclobutyl, cyclopentyl, cyclopentenyl, cyclohexyl and cyclohexenyl and the like. Exemplary bicyclic alkyl groups include bornyl, indyl, hexahydroindyl, tetrahydronaphthyl, decahydronaphthyl, bicyclo[2.1.1] hexyl, bicyclo[2.2.1]heptyl, bicyclo[2.2.1]heptenyl, 6,6-dimethylbicyclo[3.1.1]heptyl, 2,6,6-trimethylbicyclo[3.1.1] heptyl, bicyclo[2.2.2]octyl and the like. Exemplary tricyclic alkyl groups include adamantyl and the like.

The term "aryl", as used herein, includes aromatic monocyclic or multicyclic (e.g., tricyclic, bicyclic), hydrocarbon ring systems consisting of hydrogen and carbon atoms, where the ring systems may be partially saturated. Aryl groups include, but are not limited to, phenyl, tolyl, xylyl, biphenyl, naphthyl, anthracenyl, phenanthryl and tetralin.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl", as used herein, refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluoro, chloro, bromo and iodo.

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the invention can generally be prepared by conventional techniques known to those skilled in the art or by processes and methods analogous to those described herein, using an appropriate isotopically labeled reagent in place of the non-labeled reagent otherwise employed.

The first aspect of the disclosure relates to a gold(I) complex of formula (I):

or a salt thereof, a solvate thereof, a tautomer thereof, a stereoisomer thereof, or a mixture thereof, where $R_1$, $R_2$, $R_3$, and $R_4$ are independently selected from the group consisting of a hydrogen, an optionally substituted alkyl, an optionally substituted cycloalkyl, an optionally substituted alkoxy, an optionally substituted aryl, an optionally substituted arylalkyl, an optionally substituted alkanoyl, an optionally substituted aroyl, a halogen, a cyano, and a nitro;

$R_5$, $R_6$, $R_7$, $R_8$, $R_9$, $R_{10}$, $R_{11}$, and $R_{12}$ are independently selected from the group consisting of a hydrogen, an optionally substituted alkyl, an optionally substituted cycloalkyl, an optionally substituted aryl, and an optionally substituted arylalkyl; and X is an anion.

In one embodiment, the anion is a halide ion, a trifluoromethanesulfonate ion, a hexafluorophosphate ion, a tetrafluoroborate ion, or a perchlorate ion.

In one embodiment, $R_1$, $R_2$, $R_3$, $R_4$, $R_5$, $R_6$, $R_7$, $R_8$, $R_9$, $R_{10}$, $R_{11}$, and $R_{12}$ are a hydrogen, and the anion is $Cl^-$.

Previous structural studies on gold(I) complexes with amino-/imino-phosphines have revealed that gold center in these complexes is usually coordinated only by phosphorus atoms adopting a linear environment. The nitrogen atom does not bind to the metal atom (T. Traut-Johnstone et al., *J. Inorg. Biochem.* 2015, 145, 108-120; H. Chiririwa et al., *Polyhedron* 2013, 49, 29-35; and M. F. Fillat et al., *Eur. J. Inorg. Chem.* 2011, 9, 1487-1495, each incorporated herein by reference in their entirety). The gold(I) complex of the first aspect may be prepared by mixing a gold(I) precursor with a phosphine ligand, e.g. 2-(diphenylphosphino)ethanamine. Exemplary gold(I) precursors used herein include, but are not limited to, chloro(tetrahydrothiophene)gold(I), chloro(dimethyl sulfide)gold(I), bromo(tetrahydrothiophene)gold(I), and chloro(triphenylphosphine)gold(I).

As used herein, the term "solvent" includes, but is not limited to, organic solvents, e.g. alcohols such as methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, and cyclohexanol, amide solvents such as dimethylformamide, dimethylacetamide, and N-methyl-2-pyrrolidone, aromatic solvents such as benzene, o-xylene, m-xylene, p-xylene, and mixtures of xylenes, toluene, mesitylene, anisole, 1,2-dimethoxybenzene, α,α,α-trifluoromethylbenzene, and fluorobenzene, chlorinated solvents such as chlorobenzene, dichloromethane, 1,2-dichloroethane, 1,1-dichloroethane, and chloroform, ester solvents such as ethyl acetate, and propyl acetate, ethers such as diethyl ether, tetrahydrofuran, 1,4-dioxane, tetrahydropyran, t-butyl methyl ether, cyclopentyl methyl ether, and di-isopropyl ether, glycol ethers such as 1,2-dimethoxyethane, diglyme, and triglyme, acetonitrile, propionitrile, butyronitrile, benzonitrile, dimethyl sulfoxide, water, e.g. tap water, distilled water, doubly distilled water, deionized water, and deionized distilled water, and mixtures thereof. Preferably, the solvent is dichloromethane.

The phosphine ligand, e.g. 2-(diphenylphosphino)ethanamine, may be dissolved in a solvent to give a solution with a concentration in a range of 0.01-1 M, preferably 0.05-0.5 M, more preferably 0.1-0.25 M. The gold(I) precursor may be dissolved in a solvent to give a solution with a concentration in a range of 0.01-1 M, preferably 0.05-0.5 M, more preferably 0.1-0.25 M. The solution may be cooled to a temperature in a range of −15 to 5° C., preferably −5 to 0° C. The solution may be cooled with an external cooling source such as an ice bath with or without salt, or a thermostatted thermocirculator. The solution of the gold(I) precursor may be added to the solution of the phosphine ligand dropwise to form a mixture. The mixture can be agitated for about 0.5-12 hours, preferably 1-6 hours, more preferably 2-4 hours. The mixture may be agitated by stirring utilizing a magnetic stirrer, an overhead stirrer, a vortexer, or a rotary shaker, with a speed of at least 100 rpm, preferably at least 300 rpm, more preferably at least 500 rpm. In one embodiment, the mixture is agitated by mixing using a centrifugal mixer with a rotational speed of at least 250 rpm, preferably at least 500 rpm, more preferably at least 1000 rpm. In one embodiment, the mixture is mixed with a spatula. In one embodiment, the mixture is agitated by sonication. In another embodiment, the mixture is left to stand without being stirred.

The mixture may then be filtered to collect a solution. The solution may be concentrated by evaporating a solvent to yield a crude gold(I) complex of formula (I). The crude gold(I) complex of formula (I) may be further purified by methods known to those skilled in the art, for example, aqueous workup, extraction with solvents, distillation, recrystallization, column chromatography, and high-performance liquid chromatography (HPLC). Preferably, recrystallization is used to yield the gold(I) complex. Specifically, a mixture of acetone and dichloromethane is chosen for the recrystallization. The yield of the gold(I) complex is at least 40%, preferably at least 65%, more preferably at least 85% by mole, based on the total moles of the gold(I) precursor as a starting material.

The second aspect of the disclosure relates to a gold(I) dithiocarbamate polymer of formula (II):

(II)

or a salt thereof, a solvate thereof, a tautomer thereof, a stereoisomer thereof, or a mixture thereof.

where $R_{13}$, $R_{14}$, $R_{15}$, and $R_{16}$ are independently selected from the group consisting of a hydrogen, an optionally substituted alkyl, an optionally substituted cycloalkyl, an optionally substituted aryl, and an optionally substituted arylalkyl;

n is an integer between 2-10000; and with the proviso that $R_{13}$, $R_{14}$, $R_{15}$, and $R_{16}$ are not each an ethyl.

In some embodiments, $R_{13}$, $R_{14}$, $R_{15}$, and $R_{16}$ are independently an optionally substituted alkyl or an optionally substituted arylalkyl. In one embodiment, $R_{13}$, $R_{14}$, $R_{15}$, and $R_{16}$ are a methyl or a benzyl.

Formula (II) may represent the smallest repeating unit of the Au(I)—Au(I) bonded gold(I) dithiocarbamate polymeric structure, wherein n denotes the degree of polymerization.

Aurophilicity refers to the tendency of gold complexes to aggregate via formation of Au—Au bonds. The main evidence for aurophilicity is from the crystallographic analysis of Au(I) complexes (D. Paliwoda et al., *J. Phys. Chem. Lett.* 2014, 5, 2182-2188; and R. J. Roberts et al., *Chem. Commun.* 2014, 50, 3148-3150, each incorporated herein by reference in their entirety). The gold-gold bond usually has a length of about 3.0 Å and a strength of about 7-12 kcal/mol (H. Schmidbaur, *Gold Bulletin* 2000, 33, 3-10; and W. J. Hunks et al., *Inorg. Chem.* 2002, 41, 4590-4598, each incorporated herein by reference in their entirety), which is comparable to the strength of a hydrogen bond.

As used herein a "polymer" or "polymeric structure" refers to a large molecule or macromolecule, of many repeating subunits and/or substances composed of macromolecules. As used herein a "monomer" refers to a molecule or compound that may bind chemically to other molecules to form a polymer. As used herein the term "repeat unit" or "repeating unit" refers to a part of the polymer whose repetition would produce the complete polymer chain (excluding the end groups) by linking the repeating units together successively along the chain. The term "degree of polymerization" refers to the number of repeating units in a macromolecule or polymer.

In most embodiments, degree of polymerization n is an integer between 2 to 10000. Preferably, n is 2-5000, more preferably 2-4000, more preferably 2-3000, more preferably 3-2000, more preferably 3-1000, more preferably 3-500, more preferably 3-250, more preferably 4-100, more preferably 4-50, more preferably 4-25, more preferably 4-10. It is equally envisaged that values for n may fall outside of these ranges and still provide suitable polymeric structure of formula (II).

The gold(I) dithiocarbamate polymer of formula (II) of the second aspect may be prepared by mixing the gold(I) precursor described previously with a dithiocarbamate salt. Exemplary gold(I) precursors used herein include, but are not limited to, chloro(tetrahydrothiophene)gold(I), chloro(dimethyl sulfide)gold(I), bromo(tetrahydrothiophene)gold(I), and chloro(triphenylphosphine)gold(I).

The dithiocarbamate salt may be represented by the following formula:

where M$^+$ is an alkali metal cation (e.g. sodium, potassium, cesium, lithium, silver, and rubidium), an ammonium cation, an optionally substituted alkylammonium cation (e.g. dimethylammonium, diethylammonium, triethylammonium, tetrabutylammonium, tributylmethylammonium, trioctylmethylammonium, and benzylammonium cations), an optionally substituted arylammonium cation (e.g. phenylammonium, and diphenylammonium cations), or an optionally substituted alkylarylammonium cation (e.g. dimethylphenylammonium, and trimethylphenylammonium cations), and R$_x$ and R$_y$ are independently selected from the group consisting of a hydrogen, an optionally substituted alkyl, an optionally substituted cycloalkyl, an optionally substituted aryl, and an optionally substituted arylalkyl.

Exemplary dithiocarbamate salts include, without limitation, sodium dimethyldithiocarbamate, potassium dimethyldithiocarbamate, sodium diethyldithiocarbamate, potassium diethyldithiocarbamate, and sodium dibenzyldithiocarbamate.

The gold(I) precursor, e.g. chloro(dimethyl sulfide)gold(I), may be dissolved in a solvent to give a solution with a concentration of the gold(I) precursor in a range of 0.005-1 M, preferably 0.01-0.5 M, more preferably 0.05-0.25 M. The dithiocarbamate salt may be dissolved in a solvent to give a solution with a concentration of the dithiocarbamate salt in a range of 0.005-1 M, preferably 0.01-0.5 M, more preferably 0.05-0.25 M. The solution of the dithiocarbamate salt may be added to the solution of the gold(I) precursor at a temperature of 5-40° C., preferably 10-30° C., more preferably 15-25° C. to form a mixture. The mixture can be agitated at a temperature of 5-40° C., preferably 10-30° C., more preferably 15-25° C. for about 0.5-18 hours, preferably 1-12 hours, more preferably 4-8 hours. The mixture may then be agitated by stirring utilizing a magnetic stirrer, an overhead stirrer, a vortexer, or a rotary shaker, with a speed of at least 100 rpm, preferably at least 300 rpm, more preferably at least 500 rpm. In one embodiment, the mixture is agitated by mixing using a centrifugal mixer with a rotational speed of at least 250 rpm, preferably at least 500 rpm, more preferably at least 1000 rpm. In one embodiment, the mixture is mixed with a spatula. In another embodiment, the mixture is agitated by sonication. In another embodiment, the mixture is left to stand without being stirred.

The mixture may then be filtered to collect a solution. The solution may be concentrated by evaporating a solvent to yield the gold(I) dithiocarbamate polymer of formula (II). In another embodiment, the solution may be left for crystallization and yield the gold(I) dithiocarbamate polymer of formula (II). The yield of the gold(I) dithiocarbamate polymer is at least 50%, preferably at least 75%, more preferably at least 90% by weight.

The third aspect of the disclosure relates to a composition having the gold(I) complex of formula (I) of the first aspect, the salt thereof, the solvate thereof, the tautomer thereof, the stereoisomer thereof, or the mixture thereof, and a pharmaceutically acceptable carrier and/or excipient. The third aspect of the disclosure further relates to a composition having the gold(I) dithiocarbamate polymer of formula (II) of the second aspect, the salt thereof, the solvate thereof, the tautomer thereof, the stereoisomer thereof, or the mixture thereof, and a pharmaceutically acceptable carrier and/or excipient. In some embodiments, the compositions mentioned above having either the gold(I) complex of formula (I) or the gold(I) dithiocarbamate polymer of formula (II) are suitable for administering to a subject in need thereof.

As used herein, the term "composition" refers to a mixture of the active ingredient with other chemical components, such as pharmaceutically acceptable carriers and excipients. The composition may be manufactured using any of a variety of processes, including, without limitation, conventional mixing, dissolving, granulating, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

As used herein, the term "active ingredient" refers to an ingredient in the composition that is biologically active, for example, the gold(I) complex of formula (I), a salt thereof, a solvate thereof, a tautomer thereof, and a stereoisomer thereof, the gold(I) dithiocarbamate polymer of formula (II), a salt thereof, a solvate thereof, a tautomer thereof, and a stereoisomer thereof, or both.

As used herein, the phrase "pharmaceutically acceptable carrier or excipient" refers to a pharmaceutically acceptable material, composition or vehicle such as a liquid or solid filler, diluent, binder, manufacturing aid (e.g. lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Exemplary materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxy methyl cellulose, ethyl cellulose and cellulose acetate; (4) powdered tragancanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) other non-toxic compatible substances employed in pharmaceutical formulations and mixtures thereof. Non-limiting examples of specific uses of pharmaceutically acceptable carriers can be found in, e.g. "Pharmaceutical Dosage Forms and Drug Delivery Systems" (Howard C. Ansel et al., eds., Lippincott Williams & Wilkins Publishers, 7$^{th}$ edition 1999); "Remington: The Science and Practice of Pharmacy" (Alfonso R. Gennaro ed., Lippincott, Williams & Wilkins, 20$^{th}$ edition 2000); "Goodman & Gilman's The Pharmacological Basis of Therapeutics" Joel G. Hardman et al., eds., McGraw-Hill Professional, 10$^{th}$ edition, 2001); and "Handbook of Pharmaceutical Excipients" (Raymond C. Rowe et al., APhA Publications, 4$^{th}$ edition 2003), each incorporated herein by reference in their entirety.

In another embodiment, wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions described herein. Exemplary pharmaceutically acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In another embodiment, the pharmaceutically acceptable carrier or excipient is a binder. As used herein, "binders" refers to materials that hold the ingredients in a tablet together. Binders ensure that tablets and granules can be formed with the required mechanical strength, and give volume to low active dose tablets. Exemplary pharmaceutically acceptable binders include, but are not limited to: (1) saccharides and their derivatives, such as sucrose, lactose, starches, cellulose or modified cellulose such as microcrystalline cellulose, carboxy methyl cellulose, and cellulose ethers such as hydroxypropyl cellulose (HPC), and sugar alcohols such as xylitol, sorbitol or maltitol; (2) proteins such as gelatin; and (3) synthetic polymers including polyvinylpyrrolidone (PVP) and polyethylene glycol (PEG).

Binders can be classified according to their application. Solution binders are dissolved in a solvent (i.e. water or alcohol in wet granulation processes). Exemplary solution binders include, but are not limited to, gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Exemplary dry binders include, but are not limited to, cellulose, methyl cellulose, polyvinylpyrrolidone and polyethylene glycol. In terms of the present disclosure, the pharmaceutically acceptable carrier or excipient may be a solution binder, a dry binder or mixtures thereof.

In some embodiments, the pharmaceutically acceptable carrier and/or excipient used herein may be an organic solvent, an inorganic salt, a surfactant, and/or a polymer.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Surfactants that may be present in the compositions of the present disclosure include zwitterionic (amphoteric) surfactants, e.g., phosphatidylcholine, and 3-[(3-cholamidopropyl) dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinvlpyrrolidone, polyethylene glycol, polyhydroxycellulose, chitin, chitosan, and copolymers, terpolymers, or combinations or mixtures thereof.

In most embodiments, the composition has at least about 1 wt %, at least about 5 wt %, at least about 10 wt %, at least about 20 wt %, at least about 30 wt %, at least about 40 wt %$^0$, at least about 50 wt %, at least about 60 wt %, at least about 70 wt %, at least about 80 wt %, at least about 90 wt %, at least about 99 wt %, or at least about 99.9 wt % of the gold(I) complex of formula (I) of the first aspect, the salt thereof, the solvate thereof, the tautomer thereof, the stereoisomer thereof, or the combination thereof. The composition may have 0.01-100 µM, 0.1-50 µM, 1-25 µM, or 5-12.5 µM of the gold(I) complex of formula (I) relative to the total volume of the composition. In some embodiments, the composition has up to 0.1 wt %, up to 1 wt %, up to 5 wt %, or up to 10 wt % of the solvate thereof. In most embodiments, the composition further comprises pharmaceutically acceptable carriers such as buffers and/or DMSO.

In most embodiments, the composition has at least about 1 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 90 wt %, at least about 99 wt %, or at least about 99.9 wt % of the gold(I) dithiocarbamate polymer of formula (II) of the second aspect, the salt thereof, the solvate thereof, the tautomer thereof, the stereoisomer thereof, or a combination thereof. The composition may have 0.01-100 µM, 0.1-50 µM, 1-25 µM, or 5-12.5 µM of the gold(I) dithiocarbamate polymer of formula (II) relative to the total volume of the composition. In some embodiments, the composition has up to 0.1 wt %, up to 1 wt %, up to 5 wt %, or up to 10 wt % of the solvate thereof. In most embodiments, the composition further comprises pharmaceutically acceptable carriers such as buffers and/or DMSO.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

In other embodiments, the composition having the gold(I) complex of formula (I) of the first aspect, the salt thereof, the solvate thereof, the tautomer thereof, the stereoisomer thereof, or the combination thereof, and the composition having the gold(I) dithiocarbamate polymer of formula (II) of the second aspect, the salt thereof, the solvate thereof, the tautomer thereof, the stereoisomer thereof, or a combination thereof have different release rates categorized as immediate release and sustained release.

The term "immediate release" refers to the release of a substantial amount of an active ingredient immediately upon administration. Typically, an immediate release indicates a complete (100%) or less than complete (e.g. about 70% or more, about 75% or more, about 80% or more, about 85% or more, about 90% or more, about 95% or more, about 99% or more, 99.9%, or 99.9%) dissolution of an active ingredient within 1-60 minutes, 1-30 minutes, or 1-15 minutes after administration.

The term "sustained release" refers to the release of an active ingredient from a composition and/or formulation over an extended period of time. In some embodiments, a sustained release indicates a dissolution of an active ingredient over a period of time up to 30 minutes, 60 minutes, 3 hours, 12 hours, 24 hours upon administration. In one embodiment, the compositions described herein do not have a sustained release.

Solid dosage forms for oral administration may include capsules, tablets, pills, powders, and granules. In such solid dosage forms, the active ingredients are ordinarily combined with one or more adjuvants appropriate to the indicated route of administration. If administered per os, the active ingredients can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled release formulation as can be provided in a dispersion of active compound in hydroxypropylmethyl cellulose. In the case of capsules, tablets, and pills, the dosage forms can also include buffering agents such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The term "parenteral", as used herein, includes subcutaneous, intravenous, intramuscular, and intrasternal injection, or infusion techniques. For therapeutic purposes, formulations for parenteral administration can be in the form of aqueous or non-aqueous isotonic sterile injection solutions or suspensions. These solutions and suspensions can be prepared from sterile powders or granules having one or more of the pharmaceutically acceptable carriers or excipients mentioned for use in the formulations for oral administration. The active ingredients can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a pharmaceutically acceptable diluent or solvent. Among the pharmaceutically acceptable diluents and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and surfactants such as those discussed above are also useful.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

The forth aspect of the disclosure relates to a method of treating cancer, including administering the compositions of the third aspect to a subject in need of therapy. The forth aspect of the disclosure further relates to a method of treating cancer, including administering a gold(I) dithiocarbamate polymer of formula (II), (II)

or a salt thereof, a solvate thereof, a tautomer thereof, a stereoisomer thereof, or a mixture thereof, to a subject in need of therapy, where $R_{13}$, $R_{14}$, $R_{15}$, and $R_{16}$ are independently selected from the group consisting of a hydrogen, an optionally substituted alkyl, an optionally substituted cycloalkyl, an optionally substituted aryl, and an optionally substituted arylalkyl; and n is an integer between 2-10000.

As used herein, the terms "treat", "treating", and "treatment" include an administration of active ingredients, compounds, or compositions of the current disclosure to prevent, reduce, or delay the onset of the symptoms or complications of a disease, alleviating or ameliorating the symptoms or arresting or inhibiting further development of the disease. "Treating" further refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the disclosure to prevent or delay, to alleviate, or to arrest or inhibit development of the symptoms or conditions associated with cell proliferation, cancer and metastasis.

The term "therapeutic effect" refers to the reduction, elimination, or prevention of the disease, symptoms of the disease, or side effects of the disease in the subject. "Treating" or "treatment" using the methods of the invention includes preventing the onset of symptoms in a subject that can be at increased risk of immune system over-activation but does not yet experience or exhibit symptoms, inhibiting the symptoms of immune system over-activation (slowing or arresting its development), providing relief from the symptoms or side-effects of the condition, and relieving the symptoms of the condition (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

The term "subject" and "patient" are used interchangeably. As used herein, they refer to any subject for whom or which therapy, including with the compositions according to the present invention is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

A subject in need of therapy includes a subject already carrying the disease, a subject being suspected of carrying the disease, and a subject predisposed to the disease. In preferred embodiments, the subject in need of therapy is a human carrying cancer, being suspected of carrying cancer, or predisposed to cancer. In one embodiment, the cancer is at least one selected from the group consisting of lung cancer, colon cancer, and breast cancer.

Mechanistic studies have suggested that, in contrast to cisplatin, DNA is not the primary target for gold(I) based anticancer complexes. Instead, thiol/selenol containing proteins such as thioredoxin reductase (TrxRa) are the most relevant targets for bioactive gold(I) compounds (S. J. Berners-Price et al., *Metallomics*, 2011, 3, 863-873; J. C. Lima et al., *Anticancer Agents Med. Chem.* 2011, 11, 921-928; P. J. Barnard et al., *Coord. Chem. Rev.* 2007, 251, 1889-1902; A. Bindoli et al., *Coord. Chem. Rev.* 2009, 253, 1692-1707; F. Magherini et al., *J. Biol. Inorg. Chem.* 2010, 15, 573-582; M. P. Rigobello et al., *Br. J. Pharmacol.* 2002, 136, 1162-1168; C. Marzano et al., *Free Rad. Biol. Med.* 2007, 42, 872-881; and L. E. Wedlock et al., *Metallomics* 2011, 3, 917-925, each incorporated herein by reference in their entirety).

Therefore, in at least one embodiment, the subject refers to a cancer patient who has been previously treated and/or administered with cisplatin and develops cisplatin resistance due to reduced intracellular drug accumulation, overexpression of HER-2/neu and the PI3-K/Akt pathway, increase in DNA damage repair, dysfunction of tumor-suppressor p53, loss of pAMT function, and/or overexpression of antiapoptotic bcl-2.

The neoplastic activity of the tumor or cancer cells may be originated or localized in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system. Preferably, the composition may be used to treat lung cancer, colon cancer and/or breast cancer. In some embodiments, the composition is used to treat cisplatin-resistant lung cancer, colon cancer and/or breast cancer.

The terms "therapeutically effective amount" or "effective amount", as used herein, refer to a sufficient amount of the active ingredient being administered which will relieve to some extent one or more of the symptoms of the disease, disorder, or condition being treated. In some embodiments, the result is a reduction and/or alleviation of the signs, symptoms, or causes of a disease, or any other desired alteration of a biological system. For example, an "therapeutically effective amount" is the amount of the gold(I) complex of formula (I), the salt thereof, the solvate thereof, the tautomer thereof, the stereoisomer thereof, or the mixture thereof, or the amount of the gold(I) dithiocarbamate polymer of formula (II), the salt thereof, the solvate thereof, the tautomer thereof, the stereoisomer thereof, or the mixture thereof, required to provide a clinically significant decrease in disease symptoms without undue adverse side effects. In some embodiments, an appropriate "therapeutically effective amount" in an individual case is determined using techniques, such as a dose escalation study. It is understood that "an effect amount" or "a therapeutically effective amount" will be dependent on the composition administered, the mode of administration, the severity and type of the condition being treated, the subject being treated due to variation in gender, metabolism, age, body weight, and general condition of the subject. In at least one embodiment, a therapeutically effective amount of the gold(I) complex of formula (I), the salt thereof, the solvate thereof, the tautomer thereof, the stereoisomer thereof, or the mixture thereof in a range of 1-300 mg/kg, preferably 20-200 mg/kg, more preferably 50-100 mg/kg is administered per body weight of the subject. In at least one embodiment, a therapeutically effective amount of the gold(I) dithiocarbamate polymer of formula (II), the salt thereof, the solvate thereof, the tautomer thereof, the stereoisomer thereof, or the mixture thereof in a range of 1-400 mg/kg, preferably 20-300 mg/kg, more preferably 50-150 mg/kg is administered per body weight of the subject.

The compositions described herein may be formulated in a single dose, or as divided doses administered at appropriate intervals, for example, as two, three, four or more sub-doses per day. In another embodiment, the compositions may be administered in several doses at appropriate intervals. In some embodiments, the interval of time between each administration may be about 1-5 minutes, 10-30 minutes, 40-60 minutes, 1-2 hours, 3-6 hours, 8-12 hours, 13-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 4 days, 6 days or a week.

In at least one embodiment, the compositions described herein are administered along with one or more additional therapies such as radiotherapy and surgery. In one embodiment, the compositions are administered before and/or after radiotherapy at an interval of less than 12 hours, 1 day, 1 week, 2 weeks, 1 month, 2 months, 3 months, 6 months, 1 year, 2 years, or 5 years. In another embodiment, the composition is administered before and/or after surgery at an interval of less than 12 hours, 1 day, 1 week, 2 weeks, 1 month, 2 months, 3 months, 6 months, 1 year, 2 years, or 5 years.

$IC_{50}$ values may be determined by cell viability assay methods such as ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R and NCI-H69/LX20, breast cancer cell lines, e.g., MDA-MB-231, MCF7, T47D, and VP303, cervical cancer cell Lines, e.g., HeLa DH, HtTA-1, HR5, and C-41, ovarian cancer cell lines, e.g., A2780, A2780cis. OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably lung cancer, colon cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

In one embodiment, the $IC_{50}$ of the gold(I) complex of formula (I), the salt thereof, the solvate thereof, the tautomer thereof, the stereoisomer thereof, or the mixture thereof against lung cancer cells is in a range of 0.01-100 µM, preferably 1-70 µM, more preferably 30-40 µM. In another embodiment, the $IC_{50}$ of the gold(I) complex of formula (I), the salt thereof, the solvate thereof, the tautomer thereof the stereoisomer thereof or the mixture thereof against colon cancer cells is in a range of 0.01-100 µM, preferably 1-70 µM, more preferably 30-40 µM. In another embodiment, the $IC_{50}$ of the gold(I) complex of formula (I), the salt thereof, the solvate thereof, the tautomer thereof, the stereoisomer thereof, or the mixture thereof against breast cancer cells is in a range of 0.01-100 µM, preferably 1-80 µM, more preferably 30-60 µM.

In one embodiment, the $IC_{50}$ of the gold(I) dithiocarbamate polymer of formula (II), the salt thereof, the solvate thereof, the tautomer thereof, the stereoisomer thereof, or the mixture thereof against lung cancer cells is in a range of 0.01-350 µM, preferably 1-100 µM, more preferably 30-40 µM. In another embodiment, the $IC_{50}$ of the gold(I) dithiocarbamate polymer of formula (II), the salt thereof, the solvate thereof, the tautomer thereof, the stereoisomer thereof, or the mixture thereof against colon cancer cells is in a range of 0.01-300 µM, preferably 1-100 µM, more preferably 30-70 µM. In another embodiment, the $IC_{50}$ of the gold(L) dithiocarbamate polymer of formula (II), the salt thereof, the solvate thereof, the tautomer thereof, the stereoisomer thereof, or the mixture thereof against breast cancer cells is in a range of 0.01-150 µM, preferably 1-100 µM, more preferably 40-80 µM.

In most embodiments, the method further comprises detecting a mutation in a cancer biomarker and/or measuring a concentration level of a cancer biomarker before and after the administration. The term "biomarker" refers to a characteristic that is objectively measured and evaluated as an indicator of normal biological processes, pathogenic processes, or pharmacologic responses to a therapeutic intervention. The term "cancer biomarker" used herein refers to a substance secreted by a tumor or a process that is indicative of the presence of cancer in the body. Examples of cancer biomarkers include, but are not limited to HER2, BRCA1, BRCA2, Alpha-fetoprotein (AFP), AFP-L3, DCP, CYFRA 21-1, EGFR (HER1), KRAS gene, and BRAF V600. Cancer biomarkers nmay be indicative of a response towards a treatment. Examples of these indicative cancer biomarkers include, without limitation, overexpressions of CEA, NSE, CYFRA-21-1, CA-125, and CA-199 for lung cancer, overexpressions of TYMS, mutations in genes p53 and KRAS for colon cancer, and mutations in genes BRCA1 and BRCA2 for breast cancer.

The mutation in the cancer biomarker in a sample may be detected by procedures such as, without limitation, restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA).

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay.

The term "sample" used herein refers to any biological sample obtained from the subject in need of treatment for cancer including a single cell, multiple cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

In some embodiments, the biomarkers are detected and/or measured after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are provided to further illustrate protocols for synthesis and characterization within the scope of the present disclosure, and are not intended to limit the scope of the claims.

Example 1

Chemicals

Sodium tetrachloroaurate(III), sodium salts of di-alkyl/aryl dithiocarbamates (dimethyl compound as monohydrate) and dimethylsulfide were purchased from Sigma-Aldrich Co. (St. Louis, Mo., United States). 2-(Diphenylphosphino) ethylamine was obtained from Strem Chemicals Inc. (Newburyport, Mass., United States). All solvents including ethanol, diethyl ether and dichloromethane were purchased from Fluka AG, and were used without further purification.

Example 2

Measurements

Elemental analyses were obtained on a Perkin Elmer Series 11 (CHNS/O), Analyzer 2400. The solid state FT-IR spectra of the ligands and their gold(I) complexes were recorded on a Perkin Elmer FT-IR 180 spectrophotometer using KBr pellets over the range of 4000-400 $cm^{-1}$.

$^1H$ and $^{13}C$ NMR spectra were recorded on a JEOL-LA 500 MHz NMR spectrophotometer, operating at 500.0 and 125.65 MHz, respectively, using TMS as an internal reference. The $^{13}C$ NMR spectra were measured with $^1H$ broadband decoupling and spectral conditions; 32 k point data, 1 s acquisition time, 2.5 s pulse delay, and 5.12 is pulse width. $^{31}P$ NMR spectra were obtained at 200.0 MHz using phosphoric acid as an external standard. All spectra were recorded at 297 K in $CDCl_3$.

Example 3

Synthesis of the Precursor Complex $(CH_3)_2SAuCl$

The precursor complex, $(CH_3)_2SAuCl$ was synthesized by a procedure already described in the literature (M. S. Hussain et al., *J. Coord Chem.* 2000, 51, 225-234, incorporated herein by reference in its entirety). Yield 0.268 g, 90%. Anal. Calc. for $C_2H_6SAuCl$=294.55 g/mol: C, 8.35; H, 2.13; found C, 8.12; H, 1.83. $^1H$ NMR ($CDCl_3$, ppm), δ 2.75 (s, 6H). $^{13}C$ NMR ($CDCl_3$, ppm) δ 25.3.

Example 4

Synthesis of [Au(AEP)]Cl (1)

[Au(AEP)]Cl

A solution of $(CH_3)_2SAuCl$ (0.147 g, 0.5 mmol) in 5 mL dichloromethane was cooled to 5° C. and added dropwise to a solution of 2-(diphenylphosphino)ethylamine (0.115 g, 0.5 mmol) in 5 mL dichloromethane. A clear colorless solution appeared which was stirred for 1 hour and then filtered. The solution was concentrated by slow evaporation of solvent at room temperature. The product (1) was obtained as a white to cream colored solid. It was recrystallized from acetone/dichloromethane mixture and dried overnight in vacuum. The yield was 0.2 g (85° %).

Analysis for 1 ($C_{14}H_{16}AuClNP$=461.68 g/mol), Calc.: C, 36.42; H, 3.39; N, 3.03. Found: C, 35.90; H, 2.84; N, 3.36, IR ($cm^{-1}$) v(N—H) 3431, 3354; v($CH_2$) $2917_{asym}$, $2857_{sym}$, v(C—H) $1310_{bend}$; v(Ar—C=C) 1603; v(N—C) 1432. $^1H$ NMR ($CDCl_3$, ppm) δ 4.03 (s, NH); 3.31, 3.17 (m, C(1)H, H'); 2.97, 2.73 (m, C(2)H, H'); 7.45-7.65 (m, 10H, $C_5H_5$). $^{13}C$ NMR ($CDCl_3$, ppm) δ 37.65 C(1), 31.50 C(2), 129.28-133.26 C($C5H5$). $^{31}P$ NMR ($CDCl_3$, ppm) δ 21.39.

Example 5

Synthesis of [Au(AEP)$_2$]Cl (2)

[Au(AEP2)]Cl

The bis complex (2) was prepared by adding 0.115 g (0.5 mmol) 2-(diphenylphosphino)ethylamine to 0.231 g (0.5 mmol) [Au(AEP)]Cl, 1 (Au:AEP=1:2) in dichloromethane. A yellow solution appeared which was stirred for 3 hours and then filtered. The solution was concentrated by low evaporation of solvent at room temperature. A yellow solid (2) was obtained that was recrystallized from acetone/dichloromethane and dried overnight in vacuum. The yield was 0.3 g (87%).

Anal. for 2 ($C_{28}H_{32}AuClN_2P_2$=690.68 g/mol), Calc.: C, 48.67; H, 4.67; N, 4.05. Found: C, 47.89; H, 5.52; N, 4.04. IR (cm$^{-1}$) $v$(N—H) 3421, 3332; $v$(CH$_2$) 2909$_{asym}$, 2852$_{sym}$, $v$(C—H) 1275$_{bend}$; $v$(Ar—C=C) 1566; $v$(N—C) 1496. $^1$H NMR (CDCl$_3$, ppm) δ 4.04, 3.13 (s, 2H, NH); 3.02, 2.85 (m, C(1)H, H') 2.56, 1.26 (m, C(2)H, H'); 7.33-7.74 (m, 20H, C$_5$H$_5$). $^{13}$C NMR (CDCl$_3$, ppm) δ 36.63 C(1), 28.57 C(2), 129.17-133.08 C(C$_6$H$_5$). $^{31}$P NMR (CDCl$_3$, ppm) δ 26.55.

Example 6

Synthesis of gold(I)-dithiocarbamate complexes, [Au$_2$(R$_2$NCS$_2$)$_2$]$_n$ (3-5)

3: R = methyl
4: R = ethyl
5: R + benzyl

To a solution of (CH$_3$)$_2$SAuCl (0.147 g, 0.5 mmol) in 10 mL dichloromethane was added 1 equivalent of respective dithiocarbamate in 10 mL ethanol at room temperature with continuous stirring for 6 h. The reaction mixture was filtered off and the clear yellow solution was kept for slow evaporation. A yellow solid was obtained for complexes 3 and 5, while for complex 4 orange needle-like crystals were obtained.

Example 7

Spectroscopic Analysis

The IR spectra for free ligands and complexes (2-5) are summarized in Table 1. The formation of gold(I)-dithiocarbamate complexes was confirmed by the presence of the $v$(C—N) and $v$(C—SS) absorption bands. The $v$(C—N) band represented a carbon-nitrogen bond order intermediate between a single bond (v=1360-1250 cm$^1$) and a double bond (v=1690-1640 cm$^{-1}$) (M. Shahid et al., *J. Coord Chem.* 2009, 62, 62, 440-445; and M. Altaf et al., *J. Coord Chem.* 2010, 63, 1176-1185, each incorporated herein by reference in their entirety). The strong $v$(C—N) vibration of the complexes 3-5 were assigned at 1483, 1480 and 1433 cm$^{-1}$, respectively. Hence, these frequency modes suggested a partial double bond character due to partial delocalization of electron density. For the (—C—SS) stretching, two bands of medium intensity were observed at 1100, 993 cm$^{-1}$; 1098, 1067 cm$^{-1}$; and 1100, 1072 cm$^{-1}$ for 3, 4 and 5, respectively. The presence of these two bands was an indication of asymmetrical bidentate binding of dithiocarbamate ligands (R. Kellner et al., *Inorg. Chim. Acta* 1984, 84, 233, incorporated herein by reference in its entirety).

The $v$(C—H) stretching vibrations of 3 and 4 were observed at 2990 and 2970 cm$^{-1}$ respectively, while the $v$(=C—H) mode of 5 for dibenzyldithiocarbamate was detected at 3082 cm$^{-1}$. The spectra of phosphine complexes (1 and 2) displayed two bands in the region of 1620-1550 cm$^{-1}$, which were assigned to $v$(C=C) bands of the aromatic ring.

In the $^1$H NMR spectra of free ligands and their gold(I) complexes the NC—H resonances of 3, 4 and 5 appeared around 3.5, 4.0 and 5.3 ppm, respectively, as given in Table 2. The CH$_2$ protons of benzyl group were diastereotopic and therefore showed two signals. The aromatic protons of 1, 2 and 5 were observed between 7-8 ppm. The aminoethyl group gave resonances between 2-3 ppm. The $^{13}$C NMR spectra of gold(I) dithiocarbamate polymers showed significant upfield shifts with respect to free dithiocarbamate ligands. The CS$_2$ resonances of uncoordinated dithiocarbamate were observed in the range of 206-213 ppm, while in complexes, they appeared in the range, 196-210 ppm. Similarly, in phosphine complexes, upfield shifts were also observed in aromatic and aminoethyl resonances. The $^{31}$P NMR chemical shifts for complexes 1 and 2 showed significant shifts towards upfield region as shown in Table 3.

Anal. for 3 (Au$_2$(C$_2$H$_6$NCS$_2$)$_2$=634.37 g/mol), Calc.: C, 11.37; H, 2.06; N, 3.85. Found: C, 11.36; H, 1.91; N, 4.42. IR (cm$^{-1}$) $v$(C—H) 2990, $v$(C—H) 1375$_{bend}$; $v$(N—C) 1483; $v$(C=S) 1100, 993. $^1$H NMR (CDCl$_3$, ppm) δ 3.55 (s, 6H, CH$_3$). $^{13}$C NMR (CDC$_3$, ppm) δ 196.12 —NCS$_2$(1), 46.64 C(2).

Anal. for 4 (Au$_2$(C$_4$H$_{10}$NCS$_2$)$_2$=690.47 g/mol), Calc.: C, 17.72; H, 2.56; N, 3.88. Found: C, 17.39; H, 2.92; N, 4.06. IR (cm$^{-1}$) $v$(C—H) 2970, $v$(C—H) 1377$_{bend}$; $v$(—CH$_2$) 2925$_{asym}$, 2856$_{sym}$; $v$(—CH$_2$)$_{bend}$ 1264; $v$(N—C) 1480; $v$(C=S) 1098, 1067. $^1$H NMR (CDC$_3$, ppm) δ 3.92 (t, 6H, CH$_3$), (t, 4H, CH$_2$CH$_3$). $^{13}$C NMR (CDCl$_3$, ppm) δ 205.58 —NCS$_2$(I), 49.35 C(2), 12.20 C(3).

Anal. for 5 (Au$_2$(C$_{14}$H$_{14}$NCS$_2$)$_2$=926.74 g/mol), Calc.: C, 36.33; H, 2.56; N, 2.88. Found: C, 37.58; H, 3.05; N, 3.02. IR (cm$^{-1}$) $v$(CH$_2$) 2923$_{asym}$, 2850$_{sym}$, $v$(C—H) 1265$_{bend}$; $v$(Ar—C=C) 1602; $v$(N—C) 1433; $v$(C=S) 1100, 1072. $^1$H NMR (CDCl$_3$, ppm) δ 4.85, 4.78 (d, 4H, CH$_2$), 7.17-7.77 (m, 10H, C$_5$H$_5$). $^{13}$C NMR (CDCl$_3$, ppm) δ 210.80 —NCS$_2$(1), 54.27 C(2), 128.58-140.93 C(C$_6$H5).

TABLE 1

| | | | Mid FT-IR frequencies (cm$^{-1}$) for free ligands and complexes (1-5) | | | | |
|---|---|---|---|---|---|---|---|
| Free ligand/ complex | Stretch NH | Stretch C—H | Stretch =C—H | Stretch C—H(CH$_2$) | Bend C—H(CH$_2$) | Stretch Ar(C=C) | Stretch N—C | Stretch C=S |
| DMDTC | — | 2952 | — | — | — | — | 1488 | 926 |
| DEDTC | — | 2948 | — | 2979 asym | 1379 | — | 1466 | 986 |

TABLE 1-continued

Mid FT-IR frequencies (cm$^{-1}$) for free ligands and complexes (1-5)

| Free ligand/ complex | Stretch NH | Stretch C—H | Stretch =C—H | Stretch C—H(CH$_2$) | Bend C—H(CH$_2$) | Stretch Ar(C=C) | Stretch N—C | Stretch C=S |
|---|---|---|---|---|---|---|---|---|
| DBDTC | — | — | 3099 | 2922 asym | 1347 | 1600 | 1445 | 985 |
| 1 | 3431, 3354 | — | 3087 | 2917 asym 2857 sym | 1310 | 6031 | 1432 | — |
| 2 | 3421, 3332 | — | 3085 | 2909 asym 2852 sym | 1275 | 1599 | 1496 | — |
| 3 | — | — | — | 2990 asym | 1485 | — | 1483 | 1100, 993 |
| 4 | — | 2970 | — | 2925 asym 2856 sym | 1264 | — | 1480 | 1098, 1067 |
| 5 | — | 2923 | 3082 | 2923 asym 2850 sym | 1265 | 1602 | 1433 | 1100, 1076 |

DMDTC = dimethyldithiocarbamate
DEDTC = diethyldithiocarbamate
DBDTC = dibenzyldithiocarbamate

TABLE 2

$^1$H NMR chemical shifts (ppm) for free ligands and gold(I) complexes (1-5)

| Free ligand/ complex | H-1, H-1' | H-2, H-2' | H-4 | H-5 | NH | Aromatic-Hs |
|---|---|---|---|---|---|---|
| DMDTC | — | — | 3.35 | — | — | — |
| DEDTC | — | — | 3.93 | 1.13 | — | — |
| DBDTC | — | — | 5.31, 4.77 | — | — | 7.39, 7.32, 7.24 |
| AEP | 2.78, 2.77 | 2.19, 2.16 | — | — | 1.3 | 7.40, 7.38, 7.25 |
| 1 | 3.31, 3.17 | 2.97, 2.73 | — | — | 4.03 | 7.65, 7.45 |
| 2 | 3.02, 2.85 | 2.56, 1.26 | — | — | 4.04, 3.13 | — |
| 3 | — | — | 3.55 | — | — | — |
| 4 | — | — | 3.92 | 1.32 | — | — |
| 5 | — | — | 4.85, 4.78 | — | — | 7.77, 7.43, 7.32, 7.17 |

TABLE 3

$^{13}$C and $^{31}$P NMR chemical shifts (ppm) for free ligands and gold(I) complexes (1-5)

| Free ligand/ complex | C-1* | C-2 | C-SS | C-4 | C-5 | Aromatic-Cs | P$^{31}$ |
|---|---|---|---|---|---|---|---|
| DMDTC | — | — | 208.3 | 46.7 | — | — | — |
| DEDTC | — | — | 206.4 | 49.5 | 12.1 | — | — |
| DBDTC | — | — | 213.1 | 56.9 | — | — | — |
| AEP | 38.9 | 32.6 | — | — | — | 137.2-127.5 | −23.46 |
| 1 | 37.7 | 31.5 | — | — | — | 138.4-128.0 | 21.39 |
| 2 | 36.6 | 28.6 | — | — | — | 133.1-129.2 | 26.55 |
| 3 | — | — | 196.1 | 46.6 | — | — | — |
| 4 | — | — | 205.7 | 49.4 | 12.2 | — | — |
| 5 | — | — | 210.8 | 54.3 | — | — | — |

*C-1 represents carbon atom next to nitrogen

Example 8

MTT Assay for In Vitro Cytotoxicity of Complexes 1-5

The anticancer activity of complexes 1-5 was measured using a similar testing protocol reported earlier (M. Altaf et al., New J. Chem. 2015, 39, 377-385, incorporated herein by reference in its entirety) against a panel of representative human tumor cell lines, which included MCF7 (human breast cancer), HCT15 (human colon adenocarcinoma) and A549 (human lung carcinoma) cell lines. The cells were seeded at 3×10$^3$ cells/well in 100 μL DMEM containing 10% Fetal Bovine Serum (FBS) in 96-well tissue culture plate and incubated for 72 h at 37° C., 5% CO$_2$ in air and 90% relative humidity in CO$_2$ incubator. After incubation, 100 μL of 50, 25 and 12.5 μM solutions of cisplatin and complexes 1-5 prepared in Dulbecco's Modified Eagle's Medium (DMEM), were added to the cells and the cultures were incubated for 24 h. The medium of wells was discarded and 100 μL DMEM containing MTT (0.5 mg/mL) was added to the wells and incubated in CO$_2$ incubator at 37° C. in dark for 4 h. After incubation, a purple colored formazan produced in the cells appeared as dark crystals in the bottom of the wells. The culture medium was discarded from each well carefully to prevent disruption of monolayer and 100 μL of dimethyl sulfoxide (DMSO) was added in each well. The solution in the wells was thoroughly mixed to dissolve the formazan crystals which produce a purple solution. The absorbance of the 96 well-plates was taken at 570 nm with Lab systems Multiskan EX ELISA reader against a reagent blank. The experimental results were presented as micromole concentration of 50% cell growth inhibition (IC$_{50}$) of each compound. The MTT assay was performed in three independent experiments.

Example 9

In Vitro Cytotoxic Activities of Gold(I) Complexes 1-5

Figure 1:
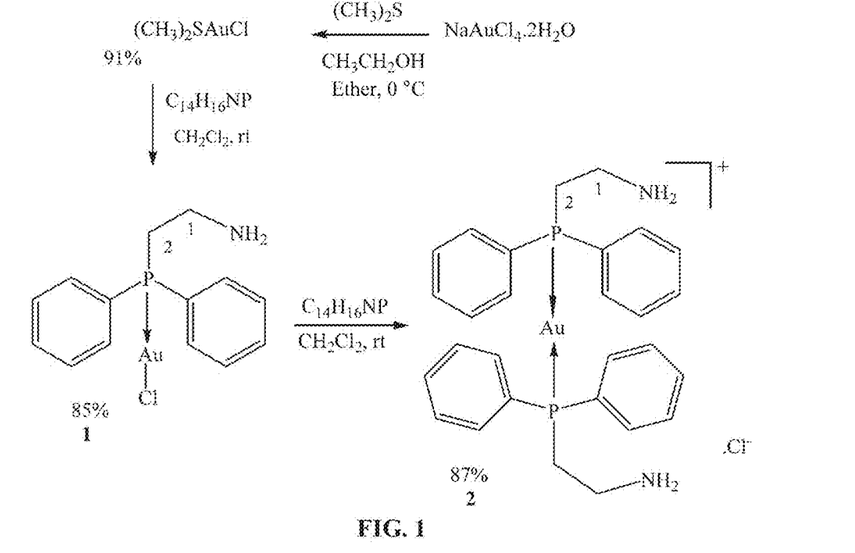
FIG. 1 shows the synthesis and structures of gold(I) complexes 1 and 2.
Figure 2:
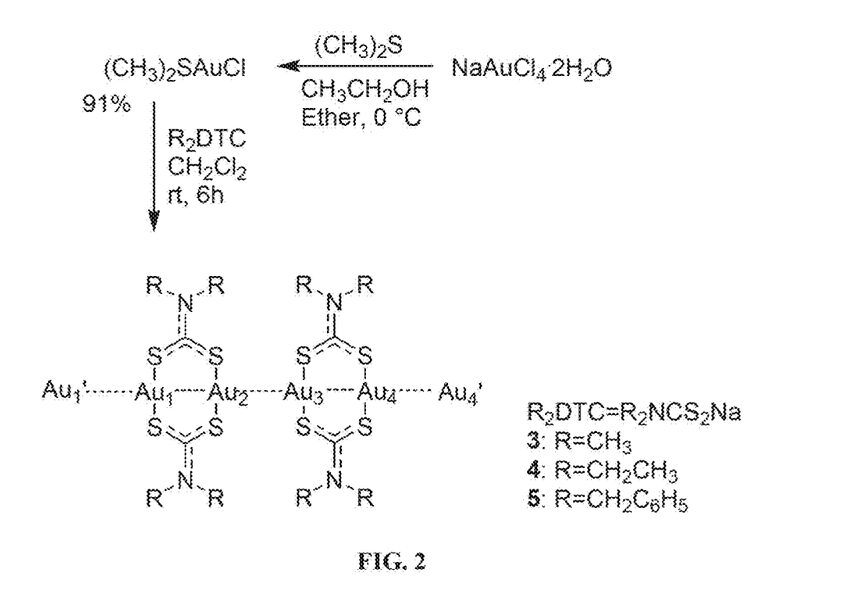
FIG. 2 shows the synthesis of gold(I)-dithiocarbamate polymers (3-5).
Figure 3:
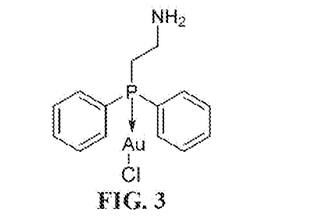
FIG. 3 shows the chemical structure of gold(I) complex 1. [Au(AEP)]Cl.
Figure 4:
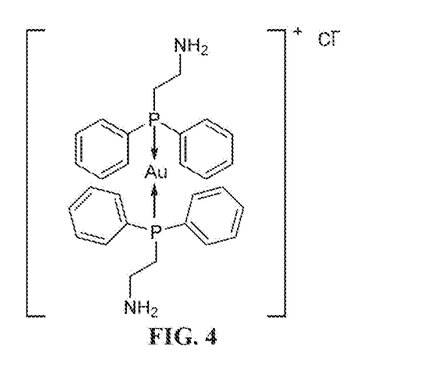
FIG. 4 shows the chemical structure of gold(I) complex 2, [Au(AEP)$_2$]Cl.
Figure 5:
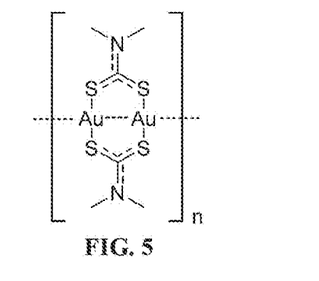
FIG. 5 shows the chemical structure of gold(I) dithiocarbamate polymer 3, [Au$_2$(S$_2$CN(CH$_3$)$_2$)$_2$]$_n$.
Figure 6:
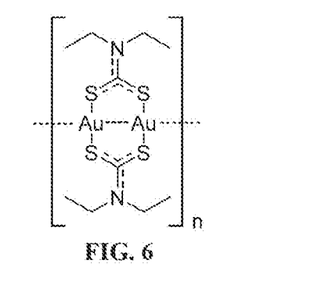
FIG. 6 shows the chemical structure of gold(I) dithiocarbamate polymer 4. [Au$_2$(S$_2$CN(C$_2$H$_5$)$_2$)$_2$]$_n$.
Figure 7:
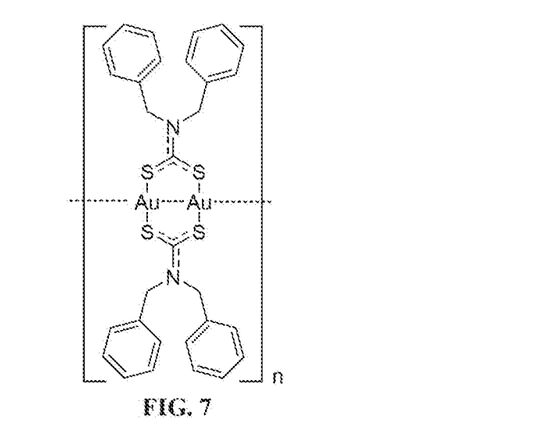
FIG. 7 shows the chemical structure of gold(I) dithiocarbamate polymer 5. [Au$_2$(S$_2$CN(C$_7$H$_7$)$_2$)$_2$]$_n$.
Figure 8:
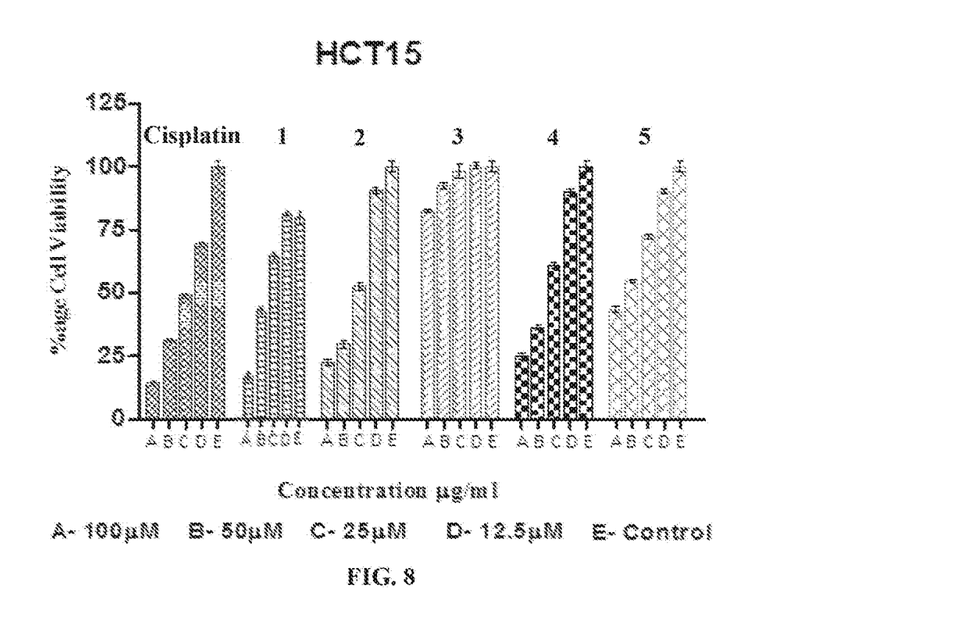
FIG. 8 is a bar graph showing the concentration dependent in vitro cytotoxicity of complexes (1-5) on the viability of HCT15 cancer cells.
Figure 9:
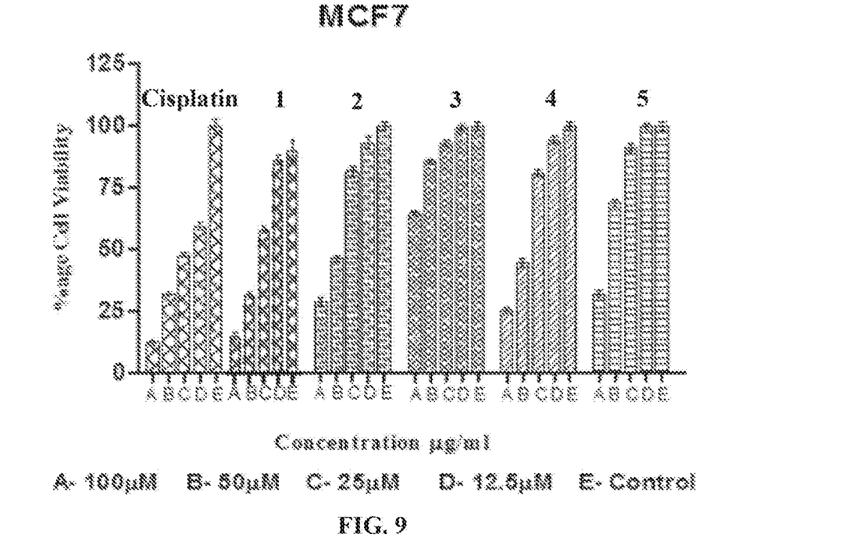
FIG. 9 is a bar graph showing the concentration dependent in vitro cytotoxicity of complexes (1-5) on the viability of MCF7 cancer cells.
Figure 10:
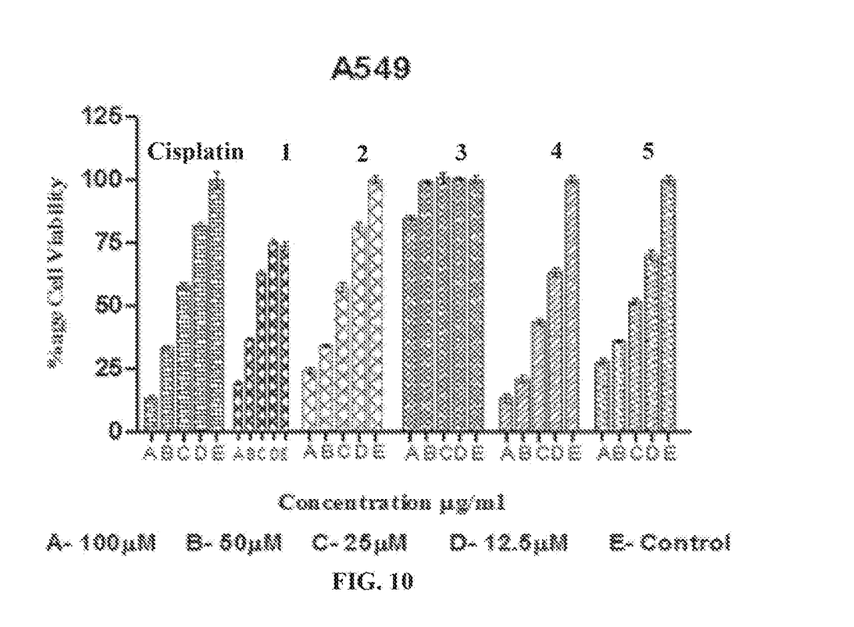
FIG. 10 is a bar graph showing the concentration dependent in vitro cytotoxicity of complexes (1-5) on the viability of A549 cancer cells.

The synthesized gold(I)-phosphine complexes (1 and 2), gold(I)-dithiocarbamates (3-5) and cisplatin (standard classical anticancer drug) were tested for in vitro cytotoxicity against A549, MCF7 and HCT15 human cancer cell lines using MTT assay. The dose-dependent inhibition of cell proliferation was obtained by specific increase in concentration of tested compounds against fixed number of three human cancer cell lines. The graphical representations of results are given in FIGS. 8-10. The IC$_{50}$ values obtained from the curve of the concentration versus percentage of cell viability are given in Table 4. It could be seen that the IC$_{50}$ values of complexes 2, 4 and 5 (34.42±1.02, 19.56±0.85, 29.25±1.81 μM respectively) for A549 cells were lower than that of cisplatin (42.2±2.01 μM). These results suggested that the anticancer effect of these compounds was better than that exhibited by cisplatin. The antiproliferative potential of 2 and 4 for HCT15 cells was also comparable to cisplatin, while for MCF7 cells it was about half with respect to cisplatin. The complex 3 was much less potent as compared to cisplatin. Its $IC_{50}$ values were the highest among the investigated complexes and showing that it was the least effective for all the studied cells. The complex 4 was the most active among the series against all three cell lines. The highest activity of 4 might be attributed to the strong binding of dithiocarbamate sulfur to gold(I) that would prevent it to interact with plasma proteins in tissues, unlike cisplatin which was strongly bound to plasma proteins through sulfur atoms of thiols (S. Ahmad, *Chem. Biodiv.* 2010, 7, 543-566, incorporated herein by reference in its entirety). It had also been observed that the gold-dithiocarbamates were more effective for A549 cells, while gold-phosphine complexes exhibited greater cytotoxicity against MCF7 cells. These findings suggested that the activity of the complexes depended on the types of cancer cells along with the structure and composition of the complexes.

TABLE 4

$IC_{50}$ values (μM) of cisplatin and gold(I) complexes (1-5) against HCT15, A549 and MCF7 cancer cell lines.

| Complex | HCT15 | A549 | MCF7 |
|---|---|---|---|
| cisplatin | 32.00 ± 2.12 | 42.20 ± 2.01 | 23.25 ± 3.79 |
| 1 | 51.21 ± 0.83 | 53.97 ± 0.94 | 38.34 ± 0.22 |
| 2 | 34.19 ± 2.49 | 34.42 ± 1.02 | 51.73 ± 2.25 |
| 3 | 256.63 ± 3.39 | 304.17 ± 5.9 | 138.82 ± 4.51 |
| 4 | 38.92 ± 2.38 | 19.56 ± 0.85 | 48.75 ± 1.96 |
| 5 | 69.07 ± 3.35 | 29.25 ± 1.81 | 76.32 ± 2.52 |

The invention claimed is:

1. A method of treating cancer, comprising:
administering a gold/cis-platin composition to a subject in need of therapy of at least one of lung cancer, colon cancer, and breast cancer, wherein the gold/cis-platin composition comprises cisplatin and a gold(I) complex of formula (I):

or a salt thereof, a tautomer thereof, a stereoisomer thereof, or a mixture thereof,
wherein $R_1$, $R_2$, $R_3$, and $R_4$ are independently selected from the group consisting, of a hydrogen, an optionally substituted alkyl, an optionally substituted alkoxy, and a nitro;
$R_5$, $R_6$, $R_7$, $R_8$, $R_9$, $R_{10}$, $R_{11}$, and $R_{12}$ are independently selected from the group consisting of a hydrogen, an optionally substituted alkyl; and
X is an anion.

2. The method of claim 1, wherein the cancer is resistant to cisplatin.

3. The method of claim 1, wherein 1-300 mg/kg of gold(I) complex of formula (I) is administered per body weight of the subject.

* * * * *